(12) United States Patent
Kapadia

(10) Patent No.: US 10,667,877 B2
(45) Date of Patent: Jun. 2, 2020

(54) CONTROLLING ROBOTIC SURGICAL INSTRUMENTS WITH BIDIRECTIONAL COUPLING

(71) Applicant: Covidien LP, Mansfield, MA (US)

(72) Inventor: Jaimeen Kapadia, Cambridge, MA (US)

(73) Assignee: Covidien LP, Mansfield, MA (US)

( * ) Notice: Subject to any disclaimer, the term of this patent is extended or adjusted under 35 U.S.C. 154(b) by 300 days.

(21) Appl. No.: 15/579,430

(22) PCT Filed: Jun. 16, 2016

(86) PCT No.: PCT/US2016/037762
§ 371 (c)(1),
(2) Date: Dec. 4, 2017

(87) PCT Pub. No.: WO2016/205452
PCT Pub. Date: Dec. 22, 2016

(65) Prior Publication Data
US 2018/0140366 A1 May 24, 2018

Related U.S. Application Data

(60) Provisional application No. 62/181,912, filed on Jun. 19, 2015.

(51) Int. Cl.
*B25J 17/00* (2006.01)
*B25J 17/02* (2006.01)
(Continued)

(52) U.S. Cl.
CPC .............. *A61B 34/35* (2016.02); *A61B 17/29* (2013.01); *A61B 34/30* (2016.02); *A61B 34/70* (2016.02);
(Continued)

(58) Field of Classification Search
CPC .......... A61B 34/30; A61B 2017/00477; A61B 2034/305; A61B 34/70
See application file for complete search history.

(56) References Cited

U.S. PATENT DOCUMENTS 5,397,323 A 3/1995 Taylor et al.
5,824,007 A 10/1998 Faraz et al.
(Continued)

FOREIGN PATENT DOCUMENTS

CN 101862223 A 10/2010
CN 101919739 A 12/2010
(Continued)

OTHER PUBLICATIONS

Supplementary European Search Report issued in European Application No. 16812394.1 dated Jan. 31, 2019, 8 pages.
(Continued)

*Primary Examiner* — Jake Cook
(74) *Attorney, Agent, or Firm* — Carter, DeLuca & Farrell, LLP

(57) ABSTRACT

A surgical system for connection to a robotic arm includes an instrument drive unit and a surgical instrument detachably coupled to the instrument drive unit. The instrument drive unit includes a motor assembly and an adapter assembly. The motor assembly has a motor and a shaft extending from the motor. The adapter assembly includes an adapter body and a tab lock supported by the adapter body. The adapter body is connected to the shaft and movable along the shaft. The surgical instrument supports an instrument tab that is engagable with the tab lock to move the tab lock relative to the adapter body from a first position to a second position. The tab lock moves from the second position to the first position so that the adapter assembly secures to the instrument tab.

20 Claims, 11 Drawing Sheets

(51) Int. Cl.
<table>
<tr><td>B25J 18/00</td><td>(2006.01)</td></tr>
<tr><td>A61B 34/35</td><td>(2016.01)</td></tr>
<tr><td>A61B 17/29</td><td>(2006.01)</td></tr>
<tr><td>A61B 34/30</td><td>(2016.01)</td></tr>
<tr><td>A61B 34/00</td><td>(2016.01)</td></tr>
<tr><td>A61B 17/00</td><td>(2006.01)</td></tr>
</table>

(52) U.S. Cl.
CPC ......... *A61B 17/00234* (2013.01); *A61B 34/25* (2016.02); *A61B 2017/00477* (2013.01); *A61B 2034/305* (2016.02)

(56) References Cited

U.S. PATENT DOCUMENTS

| | | |
|---|---|---|
| 6,231,526 B1 | 5/2001 | Taylor et al. |
| 6,244,809 B1 | 6/2001 | Wang et al. |
| 6,331,181 B1 | 12/2001 | Tierney et al. |
| 6,346,072 B1 | 2/2002 | Cooper |
| 6,364,888 B1 | 4/2002 | Niemeyer et al. |
| 6,413,264 B1 | 7/2002 | Jensen et al. |
| 6,451,027 B1 | 9/2002 | Cooper et al. |
| 6,461,372 B1 | 10/2002 | Jensen et al. |
| 6,491,701 B2 | 12/2002 | Tierney et al. |
| 6,565,554 B1 | 5/2003 | Niemeyer |
| 6,620,173 B2 | 9/2003 | Gerbi et al. |
| 6,723,106 B1 | 4/2004 | Charles et al. |
| 6,770,081 B1 | 8/2004 | Cooper et al. |
| 6,843,793 B2 | 1/2005 | Brock et al. |
| 6,902,560 B1 | 6/2005 | Morley et al. |
| 6,994,708 B2 | 2/2006 | Manzo |
| 7,083,615 B2 | 8/2006 | Peterson et al. |
| 7,125,403 B2 | 10/2006 | Julian et al. |
| 7,155,316 B2 | 12/2006 | Sutherland et al. |
| 7,331,967 B2 | 2/2008 | Lee et al. |
| 7,386,365 B2 | 6/2008 | Nixon |
| 7,594,912 B2 | 9/2009 | Cooper et al. |
| 7,837,674 B2 | 11/2010 | Cooper |
| 7,875,039 B2 | 1/2011 | Vohra et al. |
| 7,901,399 B2 | 3/2011 | Brock |
| 7,922,693 B2 | 4/2011 | Reis |
| 7,955,322 B2 | 6/2011 | Devengenzo et al. |
| 7,963,913 B2 | 6/2011 | Devengenzo et al. |
| 8,048,088 B2 | 11/2011 | Green et al. |
| 8,093,777 B2 | 1/2012 | Stiesdal |
| 8,105,320 B2 | 1/2012 | Manzo |
| 8,216,125 B2 | 7/2012 | Wilson et al. |
| 8,224,484 B2 | 7/2012 | Swarup et al. |
| 8,241,271 B2 | 8/2012 | Millman et al. |
| 8,257,303 B2 | 9/2012 | Moll et al. |
| 8,273,076 B2 | 9/2012 | Devengenzo et al. |
| 8,275,443 B2 | 9/2012 | Goldenberg et al. |
| 8,303,576 B2 | 11/2012 | Brock |
| 8,317,744 B2 | 11/2012 | Kirschenman |
| 8,353,897 B2 | 1/2013 | Doyle et al. |
| 8,452,447 B2 | 5/2013 | Nixon |
| 8,465,476 B2 | 6/2013 | Rogers et al. |
| 8,506,555 B2 | 8/2013 | Ruiz Morales |
| 8,602,031 B2 | 12/2013 | Reis et al. |
| 8,603,077 B2 | 12/2013 | Cooper et al. |
| 8,640,706 B2 | 2/2014 | Skora et al. |
| 8,641,663 B2 | 2/2014 | Kirschenman et al. |
| 8,668,702 B2 | 3/2014 | Awtar et al. |
| 8,708,952 B2 | 4/2014 | Cohen et al. |
| 8,720,448 B2 | 5/2014 | Reis et al. |
| 8,736,212 B2 | 5/2014 | Sandhu et al. |
| 8,746,252 B2 | 6/2014 | McGrogan et al. |
| 9,477,301 B2 | 10/2016 | Kishi |
| 2004/0049205 A1 | 3/2004 | Lee et al. |
| 2004/0220602 A1* | 11/2004 | Deng ............... A61B 17/32002 606/170 |
| 2005/0226703 A1 | 10/2005 | Konstas et al. |
| 2006/0074415 A1* | 4/2006 | Scott .................. A61B 18/1445 606/45 |
| 2007/0089557 A1 | 4/2007 | Solomon et al. |
| 2007/0185376 A1 | 8/2007 | Wilson et al. |
| 2007/0233052 A1 | 10/2007 | Brock |
| 2008/0021440 A1 | 1/2008 | Solomon |
| 2008/0046122 A1 | 2/2008 | Manzo et al. |
| 2008/0275367 A1 | 11/2008 | Barbagli et al. |
| 2009/0012534 A1 | 1/2009 | Madhani et al. |
| 2009/0248036 A1 | 10/2009 | Hoffman et al. |
| 2010/0030233 A1 | 2/2010 | Whitman et al. |
| 2010/0094312 A1 | 4/2010 | Ruiz Morales et al. |
| 2010/0130986 A1 | 5/2010 | Mailloux et al. |
| 2010/0204713 A1 | 8/2010 | Ruiz Morales |
| 2010/0234856 A1 | 9/2010 | Stoianovici et al. |
| 2010/0262162 A1 | 10/2010 | Omori |
| 2010/0331858 A1 | 12/2010 | Simaan et al. |
| 2011/0015650 A1 | 1/2011 | Choi et al. |
| 2011/0040150 A1 | 2/2011 | Govari et al. |
| 2011/0118754 A1 | 5/2011 | Dachs, II et al. |
| 2011/0213384 A1 | 9/2011 | Jeong |
| 2011/0245844 A1 | 10/2011 | Jinno |
| 2011/0282351 A1 | 11/2011 | Cooper et al. |
| 2012/0116416 A1 | 5/2012 | Neff et al. |
| 2012/0165828 A1 | 6/2012 | Duque et al. |
| 2012/0172850 A1 | 7/2012 | Kappel et al. |
| 2012/0209291 A1 | 8/2012 | Anderson et al. |
| 2012/0289973 A1 | 11/2012 | Prisco et al. |
| 2012/0296341 A1 | 11/2012 | Seibold et al. |
| 2012/0330286 A1 | 12/2012 | Seibold et al. |
| 2013/0066332 A1 | 3/2013 | Sutherland et al. |
| 2013/0110129 A1 | 5/2013 | Reid et al. |
| 2013/0131695 A1 | 5/2013 | Scarfogliero et al. |
| 2013/0144307 A1 | 6/2013 | Jeong et al. |
| 2013/0165854 A1 | 6/2013 | Sandhu et al. |
| 2013/0165946 A1 | 6/2013 | Sandhu et al. |
| 2013/0172713 A1 | 7/2013 | Kirschenman |
| 2013/0178868 A1 | 7/2013 | Roh |
| 2013/0223860 A1 | 8/2013 | Yasumoto |
| 2013/0282021 A1 | 10/2013 | Parihar |
| 2013/0317519 A1 | 11/2013 | Romo et al. |
| 2013/0325034 A1 | 12/2013 | Schena et al. |
| 2013/0331644 A1 | 12/2013 | Pandya et al. |
| 2013/0338679 A1 | 12/2013 | Rosielle et al. |
| 2014/0046340 A1 | 2/2014 | Wilson et al. |
| 2014/0052152 A1 | 2/2014 | Au et al. |
| 2014/0052155 A1 | 2/2014 | Hourtash et al. |
| 2014/0107665 A1 | 4/2014 | Shellenberger et al. |
| 2014/0148821 A1 | 5/2014 | Nakayama |
| 2014/0166023 A1 | 6/2014 | Kishi |
| 2014/0180309 A1 | 6/2014 | Seeber et al. |
| 2014/0207182 A1* | 7/2014 | Zergiebel ............ A61B 17/2841 606/205 |
| 2014/0276761 A1 | 9/2014 | Parihar et al. |
| 2014/0373652 A1* | 12/2014 | Zergiebel ................ F16H 19/02 74/89.23 |
| 2015/0297199 A1 | 10/2015 | Nicholas et al. |

FOREIGN PATENT DOCUMENTS

| | | |
|---|---|---|
| DE | 102009025013 A1 | 12/2010 |
| DE | 102012008537 A1 | 10/2013 |
| DE | 102012013242 A1 | 1/2014 |
| DE | 102012015541 A1 | 2/2014 |
| JP | 2012-504016 | 2/2012 |
| JP | 2013-034833 | 2/2013 |
| JP | 2014-505495 | 3/2014 |
| RU | 2012122482 A | 12/2013 |
| WO | 02/051329 A1 | 7/2002 |
| WO | 2010/017266 A1 | 2/2010 |
| WO | 2011/115387 A2 | 9/2011 |
| WO | 2015023730 A1 | 2/2015 |
| WO | 2016183054 A1 | 11/2016 |

OTHER PUBLICATIONS

Chinese Office Action issue in corresponding Chinese Application No. 20168003572.1 dated Mar. 13, 2020, 23 pages.

(56) References Cited

OTHER PUBLICATIONS

Japanese Office Action issued in corresponding Japanese Application No. 2017-564889 dated Mar. 16, 2020, 7 pages.

* cited by examiner

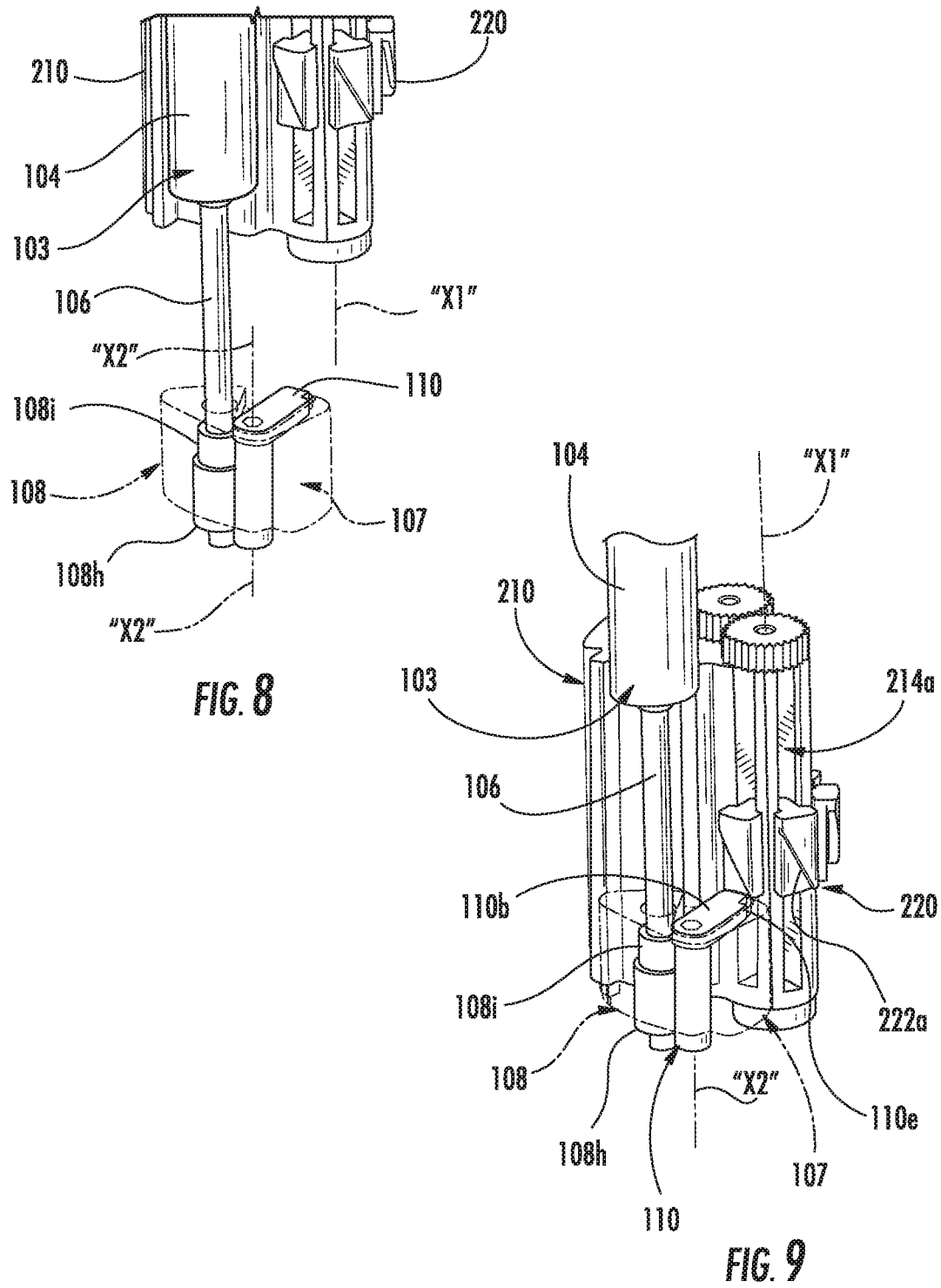

CONTROLLING ROBOTIC SURGICAL INSTRUMENTS WITH BIDIRECTIONAL COUPLING

CROSS-REFERENCE TO RELATED APPLICATIONS

This application claims the benefit of and priority to U.S. Provisional Patent Application No. 62/181,912 filed Jun. 19, 2015, the entire disclosure of which is incorporated by reference herein.

BACKGROUND

Robotic surgical systems used in minimally invasive medical procedures include a console or cart supporting a robot arm and a surgical instrument having an end effector that may include, for example, forceps, a stapler, or a grasping tool. The robot arm provides mechanical power to the surgical instrument for its operation and movement. Each robot arm may support an instrument drive unit that is operatively connected or connectable to the surgical instrument.

Prior to or during use of the robotic system, surgical instruments are selected and connected to the instrument drive units supported on the robot arm. For proper installation to be completed, certain connecting features of the surgical instrument must be matingly engaged to corresponding connecting features of the instrument drive unit. Once these features are matingly engaged, the instrument drive unit can drive the actuation of the surgical instrument. However, connection and removal of surgical instruments to instrument drive units can be difficult.

Accordingly, new robotic devices, systems, and methods that are reliable and that enable easy and efficient attachment and removal of surgical instruments is desired.

SUMMARY

The present disclosure describes robotic devices, systems, and methods that demonstrate a practical approach to meeting the performance requirements and overcoming the usability challenges associated with instrument attachment and removal. In general, the present disclosure describes robotic surgical systems that include an instrument drive unit and a surgical instrument that couples to the instrument drive unit through bidirectional coupling. The surgical instrument includes an end effector that is controllable to perform surgery in response to telemanipulation of various components of the instrument drive unit.

In accordance with one aspect of the present disclosure, there is provided a surgical system for selective connection to a robotic arm. The surgical system includes an instrument drive unit and a surgical instrument that may be removably connectable to the instrument drive unit. The instrument drive unit may have a drive unit body that defines a U-shaped opening. The U-shaped opening may be configured to receive the surgical instrument therein.

The instrument drive unit includes a motor assembly having a motor and a shaft extending from the motor. An adapter assembly may be connected to the shaft of the motor assembly and movable along the shaft. The adapter assembly may include an adapter body and a tab lock supported by the adapter body. The adapter body may define an instrument tab seat. In some embodiments, the tab lock may be rotatably supported in the adapter body. The tab lock may include a spring configured to bias the tab lock toward the first position.

The surgical instrument may include an instrument body and an end effector supported by the instrument body. The instrument body may support an instrument tab operatively associated with the end effector. The instrument tab may be engagable with the tab lock of the adapter assembly to move the tab lock relative to the adapter body of the adapter assembly from a first position to a second position as the adapter assembly moves relative to the instrument tab. The instrument tab may be configured to enable the tab lock to move from the second position to the first position so that the instrument tab secures to the adapter assembly. The instrument tab may be receivable within the instrument tab seat of the adapter body to secure the instrument tab to the adapter body. In embodiments, the adapter assembly and the instrument tab may move together while the instrument tab is secured to the adapter assembly.

In certain embodiments, the instrument tab may include an angled surface. The tab lock may be configured to cam along the angled surface of the instrument tab as the adapter assembly moves relative to the instrument tab. The tab lock may include a shoulder that contacts the angled surface of the instrument tab to rotate the tab lock relative to the adapter body as the tab lock cams along the angled surface of the instrument tab.

In some embodiments, the instrument drive unit may further include a second adapter assembly coupled to a second motor assembly. The surgical instrument may include a second instrument tab. The second adapter assembly of the instrument drive unit may be configured to secure to the second instrument tab of the surgical instrument.

According to another aspect of the present disclosure, a robotic surgical assembly includes a robotic arm, a surgical instrument, and an instrument drive unit. The surgical instrument may support an instrument tab. The instrument drive unit may be coupleable to the robotic arm.

The instrument drive unit may include a motor assembly and an adapter assembly. The motor assembly may have a motor and a shaft extending from the motor. The adapter assembly may be connected to the shaft of the motor assembly and movable along the shaft. The adapter assembly may include an adapter body and a tab lock supported by the adapter body. The tab lock may be engagable with the instrument tab of the surgical instrument to move the tab lock relative to the adapter body from a first position to a second position as the adapter assembly moves relative to the instrument tab. The tab lock may be configured to move from the second position to the first position to secure the adapter assembly to the instrument tab.

In embodiments, the first and second instrument tabs may be operatively associated with an end effector. The first and second instrument tabs may be independently movable to operate the end effector.

In accordance with yet another aspect of the present disclosure, a method for selectively coupling a surgical instrument to an instrument drive unit that is robotically controlled is provided. The method may include advancing the surgical instrument into the instrument drive unit, camming a tab lock of an adapter assembly along an instrument tab of the surgical instrument as an adapter body of the adapter assembly moves relative to the instrument tab, and rotating the tab lock of the adapter assembly relative to the adapter body of the adapter assembly to secure the instrument tab to the adapter assembly so that the instrument tab moves with the adapter assembly along a longitudinal axis of the instrument drive unit.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the disclosure given below, serve to explain the principles of the present disclosure, wherein:

FIGS. 8-14 are progressive views illustrating components of the surgical assembly of FIGS. 3 and 4 being coupled together.

DETAILED DESCRIPTION

Figure 1:
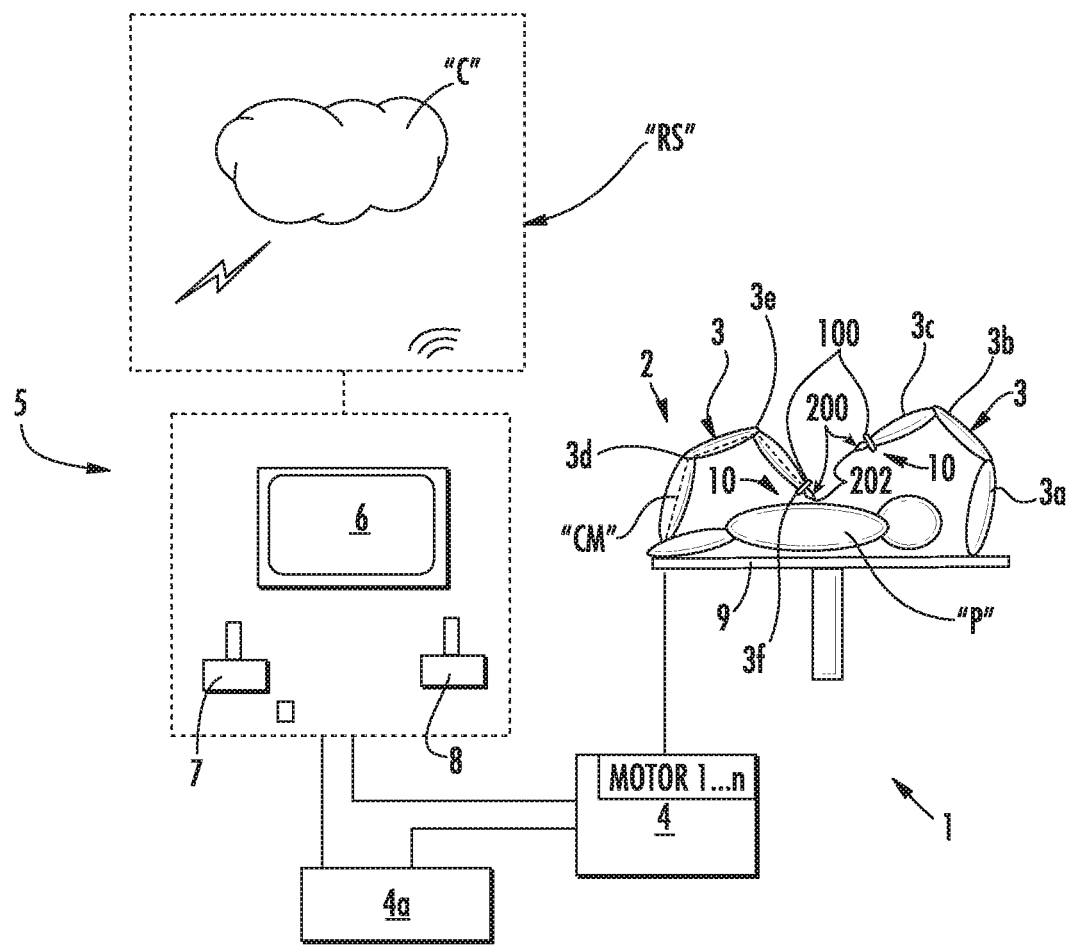
FIG. 1 is a schematic illustration of a robotic surgical system in accordance with the present disclosure.

Embodiments of the present disclosure are described in detail with reference to the drawings, in which like reference numerals designate identical or corresponding elements in each of the several views. As used herein, the term "distal" or "leading" refers to that portion of the system, assembly, device, and/or component thereof, farther from the user, while the term "proximal" or "trailing" refers to that portion of the system, assembly, device, and/or component thereof, closer to the user. As used herein, the term "clinician" refers to a doctor, nurse, or other care provider and may include support personnel. As used herein, the term "subject" refers to a human patient or other animal.

Figure 2:
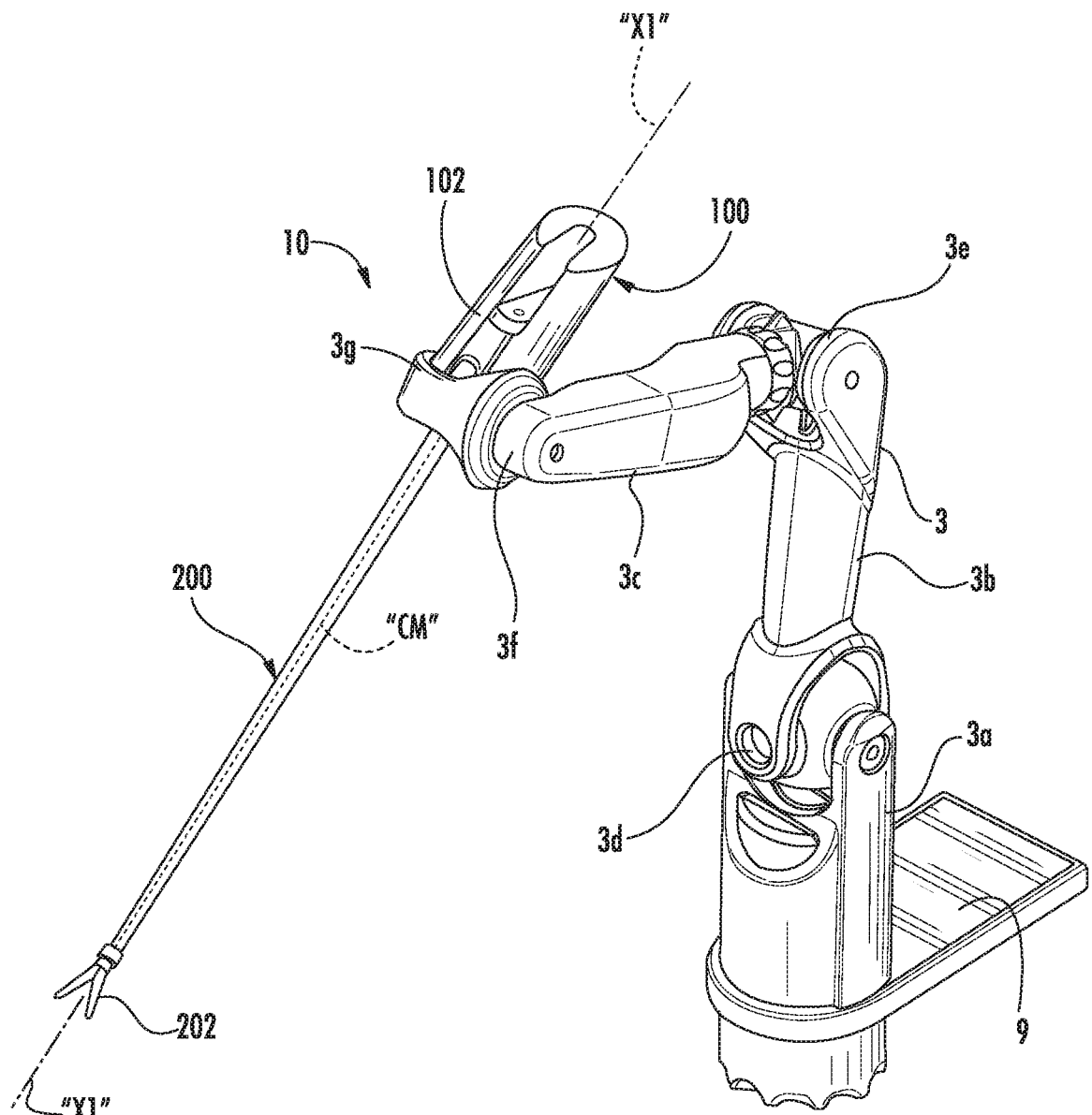
FIG. 2 is a perspective view of a robotic arm of the robotic surgical system of FIG. 1 with a surgical assembly of the robotic surgical system shown mounted on the robotic arm.

With reference to FIGS. 1 and 2, there is provided a robotic surgical system 1 including a robotic arm assembly 2 having one or more robotic arms 3. Robotic surgical system 1 further includes a control device 4 and an operating console 5 coupled with control device 4. Operating console 5 includes a display device 6 and manual input devices 7, 8, by means of which clinician is able to telemanipulate robotic arm assembly 2, or components thereof, via control device 4.

Each robotic arm 3 may include single or multiple members such as members 3a, 3b, 3c that are connected through any number of joints such as joints 3d, 3e, and 3f. Each robotic arm 3 may also include an instrument mount 3g. Robotic surgical system 1 also includes a surgical assembly 10 connected to a distal end of each robotic arm 3. Surgical assembly 10 includes an instrument drive unit 100 detachably coupled to instrument mount 3g of robotic arm 3 and a surgical instrument 200 detachably coupled to instrument drive unit 100. Surgical instrument 200 includes an end effector 202 supported at a leading or distal end thereof. Surgical instrument 200 defines a longitudinal axis "X1" therethrough that extends between leading (distal) and trailing (proximal) ends of surgical instrument 200.

Robotic arms 3 may be driven by electric drives (not shown) that are connected to control device 4. Control device 4 (e.g., a computer) is set up to activate the electric drives, for example, by a computer program, so that respective surgical assemblies 10 of robotic arms 3 execute desired movements according to movement defined by manual input devices 7, 8. Control device 4 may also be set up to regulate movement of robotic arms 3 and/or of the electric drives.

Robotic surgical system 1 is configured for use on a patient "P" lying on a patient table 9, for example, to conduct a minimally invasive procedure via end effector 202 of surgical instrument 200. Robotic surgical system 1 may include any number of robotic arms 3. Any additional robotic arms may also be connected to control device 4 and may be telemanipulatable by operating console 5 and/or control device 4. One or more additional surgical assemblies 10, instrument drive units 100, and/or surgical instruments 200 may also be attached to the additional robotic arms 3.

Control device 4 may control any number of motors (Motor 1 . . . n) configured to drive a pushing and/or a pulling of one or more connecting members "CM" (e.g., cables, rods, etc.) coupled to robotic arms 3. In use, as these connecting members "CM" are pushed and/or pulled, the connecting members "CM" effect operation and/or movement of robotic arms 3. It is contemplated that control device 4 coordinates the activation of the various motors (Motor 1 . . . n) to coordinate pushing and/or pulling motion of one or more connecting members "CM" in order to coordinate an operation and/or movement of one or more of robotic arms 3.

Control device 4 can include any suitable logic control circuit adapted to perform calculations and/or operate according to a set of instructions. Control device 4 can be configured to communicate with a remote system "RS," either via a wireless (e.g., Wi-Fi™, Bluetooth®, LTE™, etc.) and/or wired connection. Remote system "RS" can include data, instructions and/or information related to the various components, algorithms, and/or operations of robotic surgical system 1. Remote system "RS" can include any suitable electronic service, database, platform, cloud "C," or the like. Control device 4 may include a central processing unit operably connected to memory. The memory may include transitory type memory (e.g., RAM) and/or non-transitory type memory (e.g., flash media, disk media, etc.). In some embodiments, the memory is part of, and/or operably coupled to, remote system "RS."

Control device 4 can include any number of inputs and/or outputs for interfacing with the components of robotic surgical system 1, such as through a driver circuit. Control device 4 can be configured to receive input signals and/or generate output signals to control one or more of the various components (e.g., one or more motors) of robotic surgical system 1. The output signals can include, and/or can be based upon, algorithmic instructions which may be preprogrammed and/or input by a user. Control device 4 can be configured to accept any number of user inputs from a user interface (e.g., switches, buttons, touch screen, etc. of operating console 5) which may be coupled to remote system "RS."

A database 4a can be directly and/or indirectly coupled to control device 4. Database 4a can be configured to store pre-operative data from living being(s) and/or anatomical atlas(es). Database 4a may be configured to store real-time and/or intra-operative data, for example, of various conditions of one or more components of surgical system 1 (e.g., surgical assembly 10, end effector 202, connecting members "CM," etc.). Database 4a can include memory that can be part of, and/or or operatively coupled to, remote system "RS." Reference may be made to U.S. Patent Publication No. 2012/0116416, filed on Nov. 3, 2011, entitled "Medical Workstation," the entire contents of which is hereby incorporated by reference herein, for a detailed discussion of the construction and operation of a similar robotic surgical system.

Figure 3:
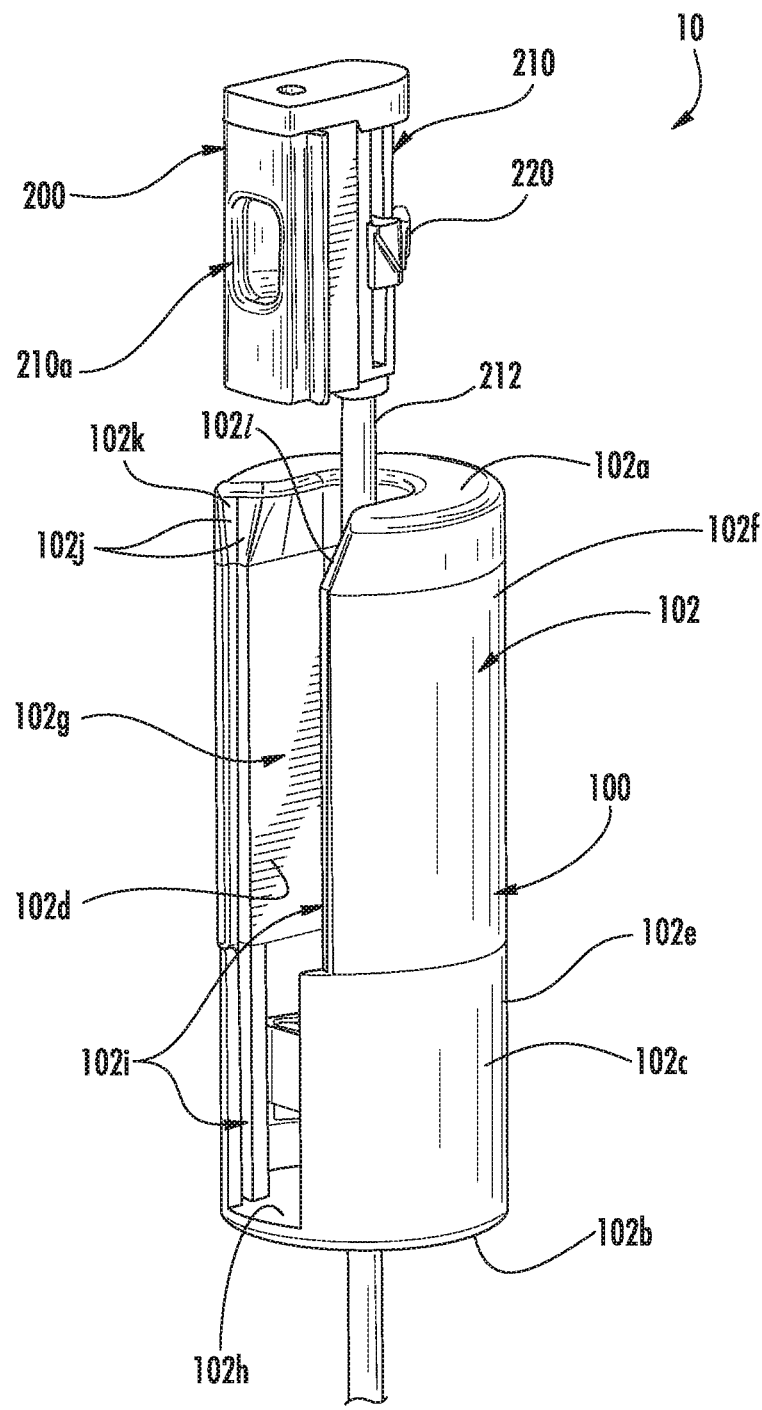
FIGS. 3 and 4 are progressive views of proximal portions of the surgical assembly of FIG. 2 showing a surgical instrument of the surgical assembly being coupled to an instrument drive unit of the surgical assembly.

With reference to FIGS. 2 and 3, instrument drive unit 100 includes a U-shaped body or housing 102. Body 102 includes an upper surface 102a, a lower surface 102b, an outer surface 102c, and an inner surface 102d. Outer and inner surfaces 102c, 102d extend between upper and lower surfaces 102a, 102b to define lower and upper portions 102e, 102f of body 102. Inner surface 102d defines a U-shaped channel 102g that extends from upper surface 102a, through upper and lower portions 102e, 102f, to a floor 102h formed in lower portion 102e of body 102. U-shaped channel 102g is configured to receive surgical instrument 200 therein. Floor 102h defines a central aperture (not shown) therethrough that opens through lower surface 102b of body 102. Upper and lower portions 102e, 102f define opposed channels 102i in inner surface 102c of body 102. Each of opposed channels 102i extends longitudinally from floor 102h to a pair of tapered surfaces 102j on upper portion 102f, forming two opposed pairs of tapered surfaces 102k, 102l.

Figure 4:
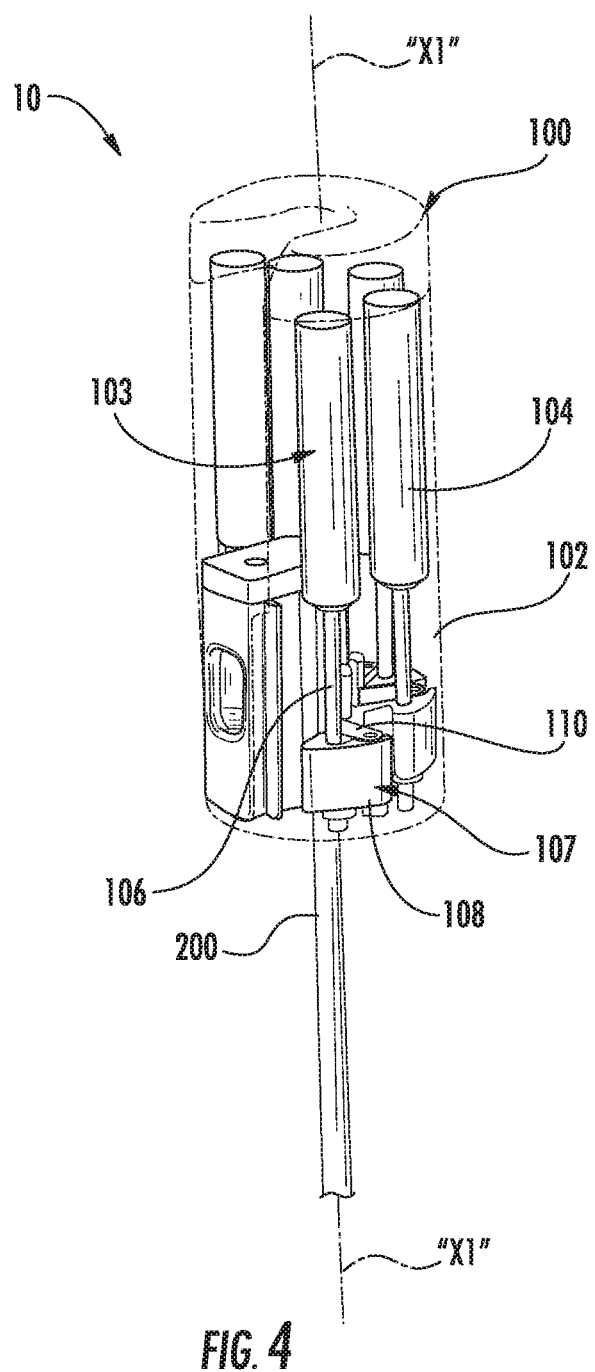

With reference to FIG. 4, instrument drive unit 100 of surgical assembly 10 further includes motor assemblies 103 supported within body 102. Each motor assembly 103 includes a motor 104 and a shaft 106 extending therefrom. An adapter assembly 107 is movably supported on shaft 106 of motor assembly 103 and includes an adapter body 108 and a tab lock 110 rotatably supported in adapter body 108. Adapter assembly 107 may be threadably coupled to shaft 106 of motor assembly 103 to enable adapter assembly 107 to axially translate along shaft 106 of motor assembly 103 as shaft 106 rotates in response to activation of motor 104 of motor assembly 103.

Figure 5:
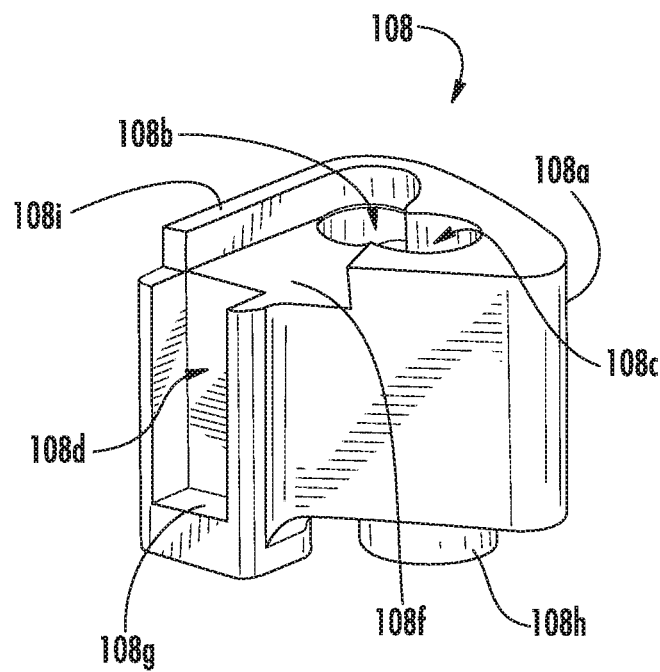
FIG. 5 is an enlarged perspective view of an adapter body of an adapter assembly of the instrument drive unit shown in FIGS. 3 and 4.

As seen in FIG. 5, adapter body 108 of adapter assembly 107 includes a block frame 108a and defines a tab lock channel 108b therethrough that is configured to receive tab lock 110 of adapter assembly 107 therein. Adapter body 108 further defines a shaft channel 108c therethrough that is configured to receive shaft 106 of motor assembly 103. Adapter body 108 defines an instrument tab seat 108d within block frame 108a and which has a bottom surface 108g that supports an instrument tab 220 (see FIGS. 7A and 7B) of surgical instrument 200. Adapter body 108 of adapter assembly 107 also includes a top support surface 108f that supports tab lock 110 of adapter assembly 107 while tab lock 110 is disposed in tab lock channel 108b of adapter body 108. Top support surface 108f of adapter body 108 includes a stop wall 108i that limits rotational movement of tab lock 110 of adapter assembly 107. One or more tube members 108h are supported in adapter body 108 of adapter assembly 107 and positioned to receive shaft 106 of motor assembly 103. Tube members 108h include threading to threadably engage threading of shaft 106 of motor assembly 103 so that adapter assembly 107 can axially translate along shaft 106 of motor assembly 103 as shaft 106 rotates in a clockwise or counterclockwise direction.

Figure 6:
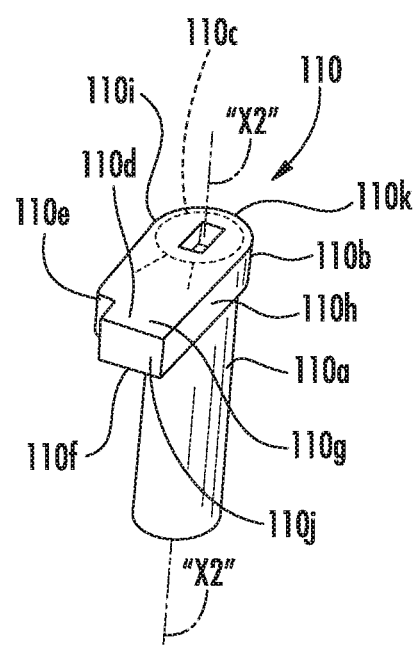
FIG. 6 is perspective view of a tab lock of the adapter assembly of the instrument drive unit shown in FIGS. 3 and 4.

With reference to FIG. 6, tab lock 110 of adapter assembly 107 includes a support leg 110a and a locking arm 110b secured to support leg 110a. Support leg 110a of tab lock 110 defines a longitudinal axis "X2" therethrough and locking arm 110b of tab lock 110 may be rotatable relative to support leg 110a about longitudinal axis "X2." In some embodiments, locking arm 110b of tab lock 110 and support leg 110a of tab lock 110 rotate together about longitudinal axis "X2." A spring 110c is supported in tab lock 110 and positioned to bias locking arm 110b against stop wall 108i of adapter body 108 while support leg 110a of tab lock 110 is disposed in tab lock channel 108b of adapter body 108. Spring 110c of tab lock 110 may be a torsion spring.

Locking arm 110b of tab lock 110 includes a finger 110d that extends distally from locking arm 110b. Locking arm 110b further includes a shoulder 110e supported adjacent to finger 110d. Shoulder 110e of locking arm 110b may be rounded and/or chamfered. Locking arm 110b includes a bottom surface 110f engaged with top support surface 108f of adapter body 108 and a top surface 110g. Locking arm 110b further includes a first side surface 110h and a second side surface 110i adjacent to shoulder 110e of locking arm 110b. Second side surface 110i of locking arm 110b is selectively engagable with stop wall 108i of adapter body 102. Locking arm 110b further includes a front surface 110j that is positioned to face surgical instrument 200 while second side surface 110i is engaged with stop wall 108i of adapter body 102, and a rear surface 110k.

Figures 7A, 7B:
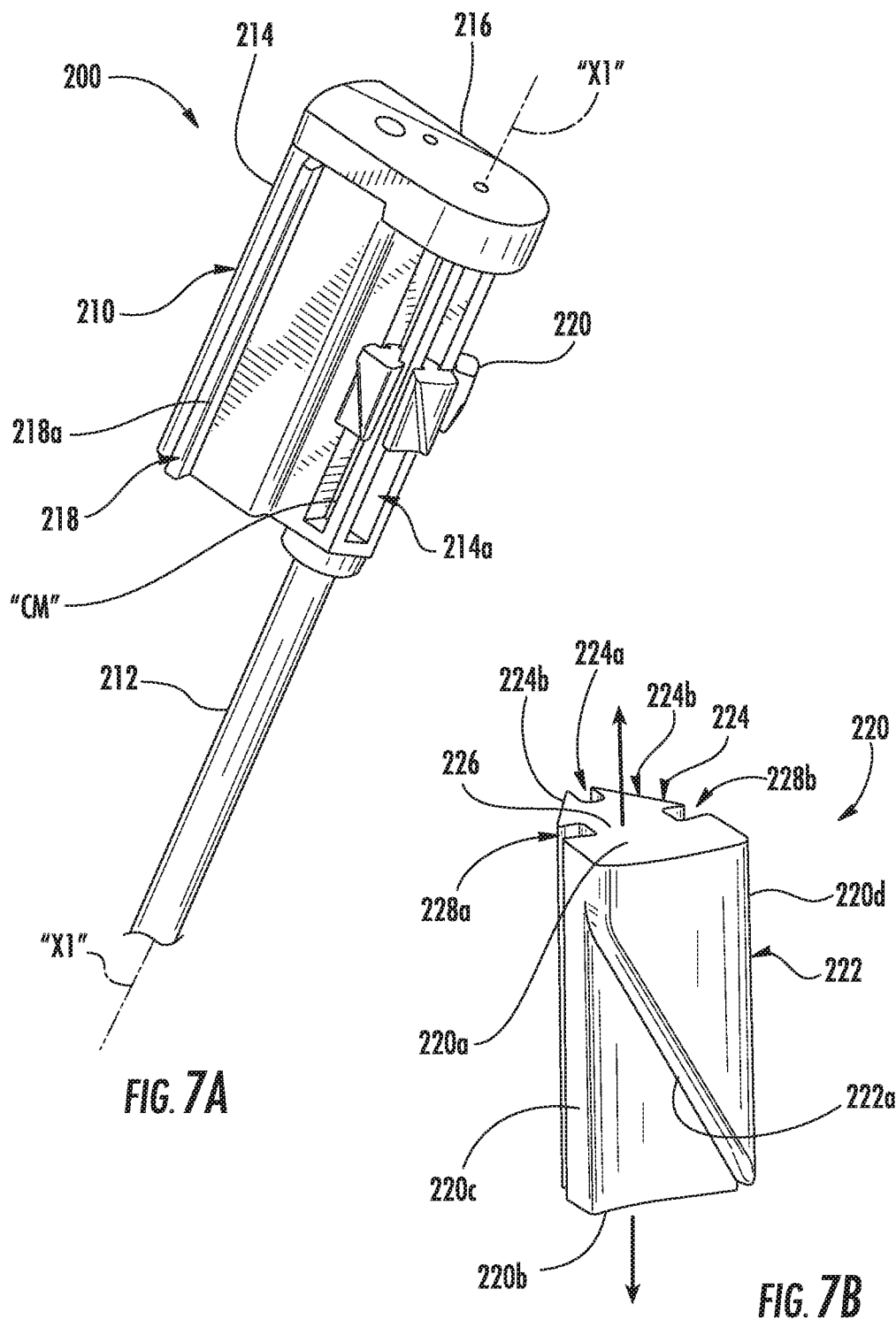
FIG. 7A is a perspective view of a proximal portion of the surgical instrument shown in FIGS. 3 and 4.
FIG. 7B is a perspective view of an instrument tab of the surgical instrument of FIG. 7A.
Figure 10A:
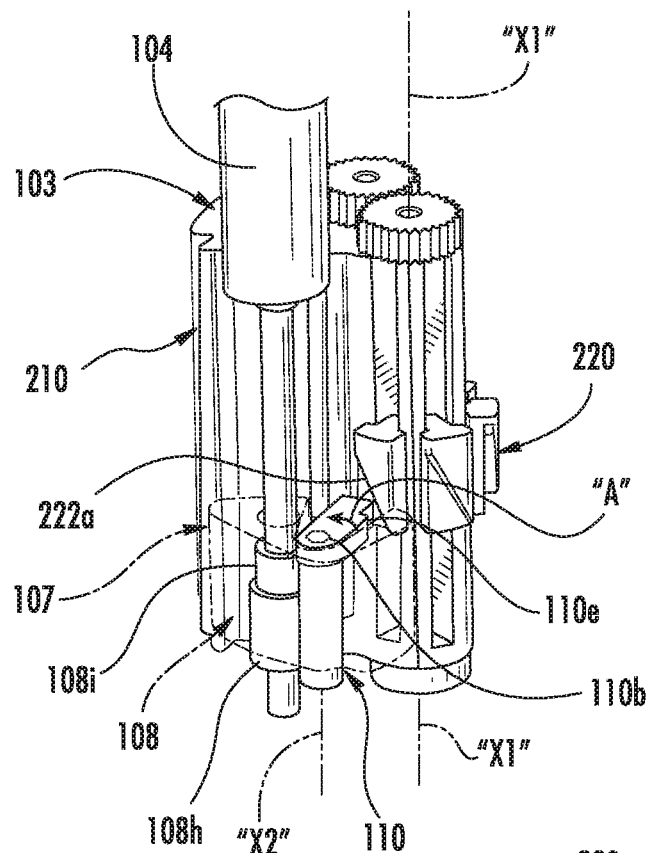
Figure 10B:
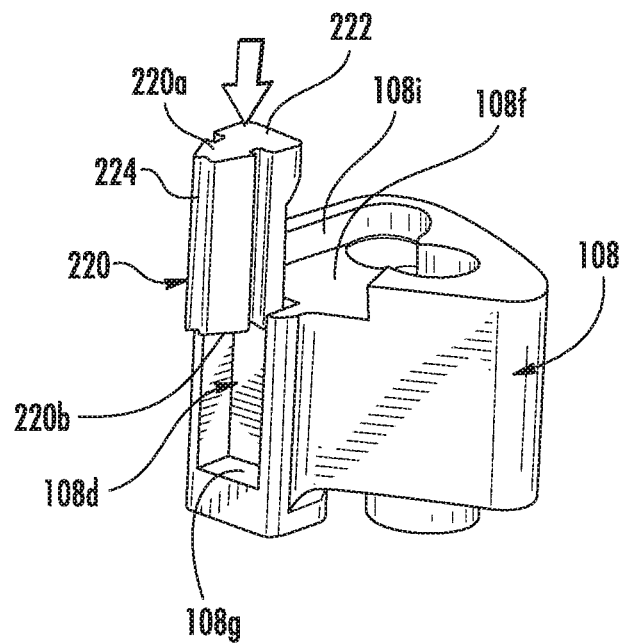
Figure 11:
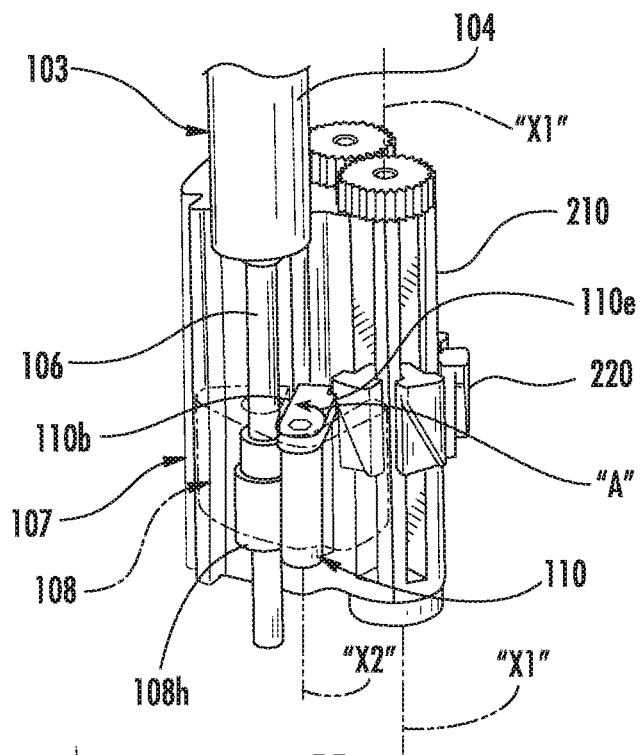
Figure 12A:
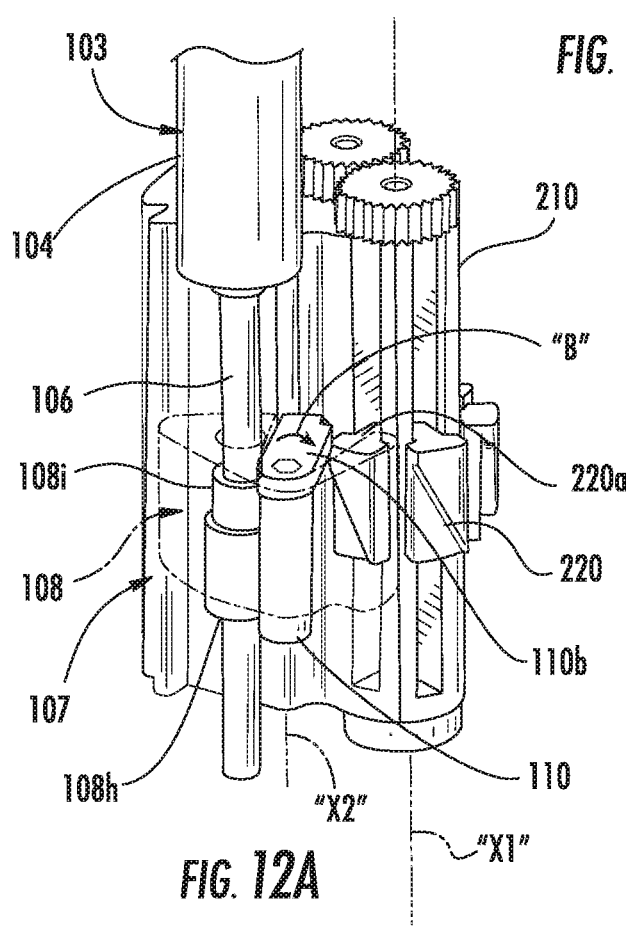
Figure 12B:
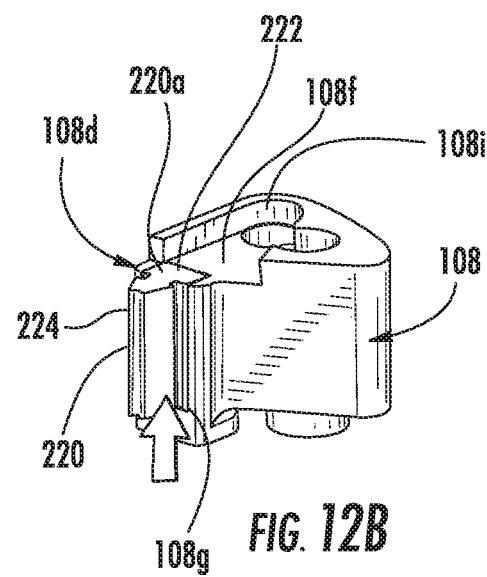

Turning now to FIGS. 7A and 7B, surgical instrument 200 of surgical assembly 10 includes an instrument body 210 and an instrument shaft 212 that extends distally from instrument body 210 to end effector 202 (see FIG. 2). Referring again briefly to FIG. 3, instrument body 210 also defines a gripping aperture 210a in instrument body 210 that can be engaged, for example, by a clinician's finger or other tool, to facilitate insertion and/or removal of surgical instrument 200 into/from instrument drive unit 100, as described in greater detail below.

With reference to FIG. 7A, instrument body 210 of surgical instrument 200 includes a body portion 214 and a head portion 216 supported on body portion 214. Body portion 214 of instrument body 210 defines channels 214a therein that extend longitudinally therealong. Body portion 214 of instrument body 210 further includes flanges 218 that extend from an outer surface thereof and longitudinally along body portion 214. Although only first flange 218a is shown in FIG. 7A, a second flange, which is similar to first flange 218a, is disposed on an opposite side of body portion 214 in mirrored relation to first flange 218a.

With reference again to FIGS. 2-4, instrument shaft 212 and end effector 202 of surgical instrument 200 are receivable through the central aperture of floor 102h of body 102 of instrument drive unit 100 as instrument body 210 of surgical instrument 200 is inserted and/or withdrawn from U-shaped channel 102g of instrument drive unit 100. Guided by the two opposed pairs of tapered surfaces 102k, 102l of instrument drive unit 100, flanges 218 of surgical instrument 100 are receivable within side channels 102i of instrument drive unit 100 to support instrument body 210 of surgical instrument 200 within U-shaped channel 102g of instrument drive unit 100. Flanges 218 are configured to maintain surgical instrument 200 in coaxial alignment with instrument drive unit 100 while flanges 218 of surgical instrument 200 are received within side channels 102i of instrument drive unit 100.

Referring again to FIGS. 7A and 7B, surgical instrument 200 further includes instrument tabs 220 slidably supported in each channel 214a of instrument body 210 of surgical instrument 200. Surgical instrument 200 may include any number of instrument tabs 220 and may define any number of channels 214a to accommodate instrument tabs 220 at spaced apart locations about body portion 214 of instrument body 210 and/or longitudinal axis "X1."

As seen in FIG. 7B, each instrument tab 220 of surgical instrument 200 includes an upper surface 220a, a lower surface 220b, a first side surface 220c, and a second side surface 220d. Instrument tab 220 includes a front face 222 and a rear face 224 that are connected by a connecting member 226. Front face 222 of instrument tab 220 defines an angled surface 222a that extends from lower surface 220b, across front face 222, and toward upper surface 220a. Rear face 224 of instrument tab 220 defines a channel 224a therethrough that receives a connecting member "CM" of surgical instrument 200 therein. Rear face 224 includes angled side surfaces 224b. A pair of side grooves 228a, 228b of instrument tab 220 is defined in first and second side surfaces 220c, 220d of instrument tab 220 between front and rear faces 222, 224 of instrument tab 220. The pair of side grooves 228a, 228b of instrument tab 220 is engagable with body portion 214 of instrument body 210 to enable a respective instrument tab 220 of surgical instrument 200 to slide axially along a respective one of channels 214a of instrument body 210.

With reference to FIGS. 3, 4, and 8-14, in order to couple adapter assemblies 107 of instrument drive unit 100 to instrument tabs 220 of surgical instrument 200, instrument body 210 of surgical instrument 200 is advanced into U-shaped channel 102g of instrument drive unit 100. As instrument body 210 of surgical instrument 200 is advanced into U-shaped channel 102g of instrument drive unit 100, flanges 218 of surgical instrument 200 slide along opposed channels 102i of instrument drive unit 100 until a bottom surface of instrument body 210 of surgical instrument 200 contacts floor 102h of instrument drive unit 100. With one or more adapter assemblies 107 of instrument drive unit 100 disposed on a lower portion of a shaft 106 of a respective motor assembly 103 of instrument drive unit 100, a motor 104 of the respective motor assembly 103 is activated to rotate shaft 106 of the respective motor assembly 103, thereby moving a respective adapter assembly 107 of the instrument drive unit 100 axially upwardly and/or away from floor 102h of instrument drive unit 100.

As seen in FIGS. 10A-12B, movement of adapter assembly 107 of instrument drive unit 100 toward motor 104 (e.g., upwardly) of motor assembly 103 causes shoulder 110e of tab lock 110 of adapter assembly 107 to contact angled surface 222a of front face 222 of instrument tab 220 of surgical instrument 200 so that shoulder 110e of tab lock 110 cams along angled surface 222a of front face 222 of instrument tab 220. As indicated by arrow "A," locking arm 110b of tab lock 110 of instrument drive unit 100 rotates about the longitudinal axis "X2" of tab lock 110 from a first position and away from stop wall 108i of adapter assembly 107 toward a second position. As locking arm 110b of tab lock 110 rotates away from stop wall 108i of adapter assembly 107, spring 110c of tab lock 110 asserts biasing forces to locking arm 110b of tab lock 110. Rotation of tab lock 110 between the first and second positions is effectuated as shoulder 110e of tab lock 110 cams along angled surface 222a of front face 222 of instrument tab 220 of surgical instrument 200.

While locking arm 110b of tab lock 110 of instrument drive unit 100 rotates away from the first position (e.g., an initial position) against stop wall 108i of adapter body 108 of adapter assembly 107, instrument tab 220 of surgical instrument 200 is received within instrument tab seat 108d of adapter assembly 107. In a fully seated position, lower surface 220b of instrument tab 220 of surgical instrument 200 contacts bottom surface 108g of instrument tab seat 108d of adapter assembly 107. Once instrument tab 220 of surgical instrument 200 is fully seated within instrument tab seat 108d of instrument drive unit 100 and bottom surface 110f of locking arm 110b of tab lock 110 of adapter assembly 107 has risen above upper surface 220a of instrument tab 220 of surgical instrument 200, biasing forces from spring 110c of tab lock 110 rotate locking arm 110b of tab lock 110 over instrument tab 220 of surgical instrument 200, as indicated by arrow "B," from the second position of tab lock 110 back toward the first position of tab lock 110 (e.g., against stop wall 108i of adapter body 108).

Figure 13:
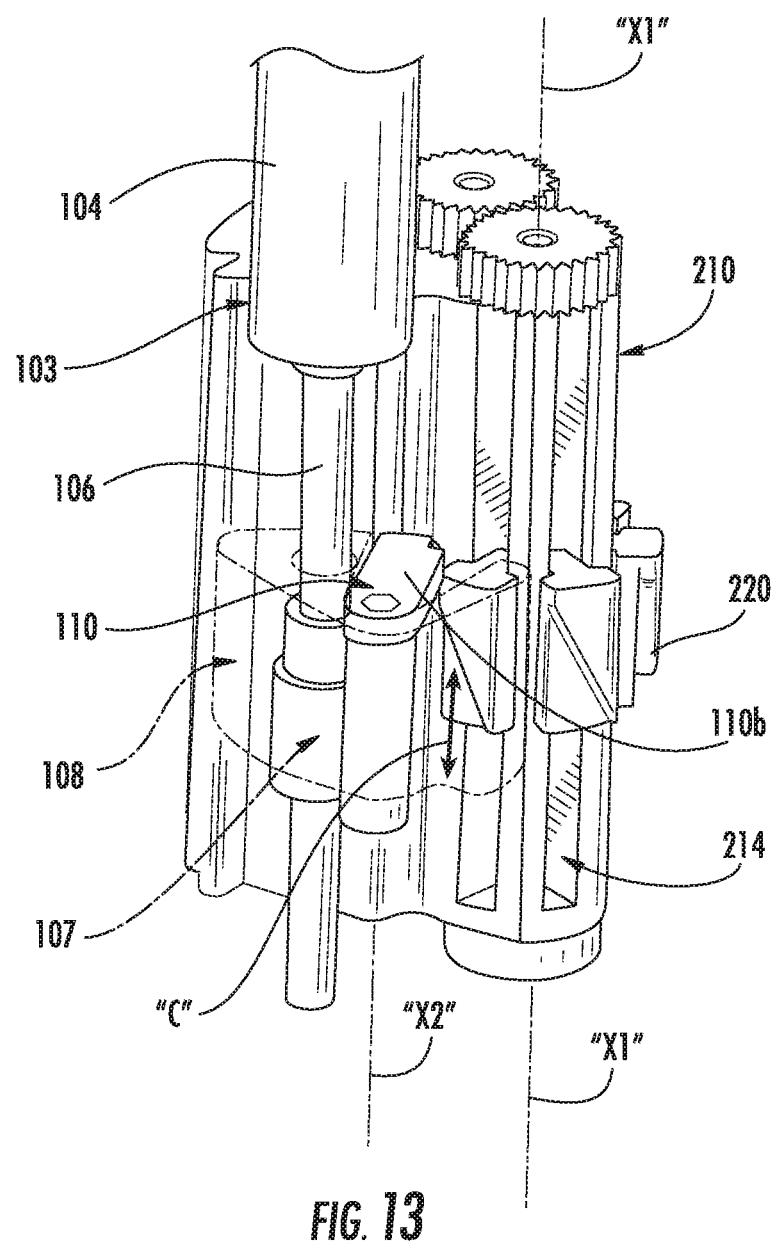

With reference to FIG. 13, once locking arm 110b of tab lock 110 of instrument drive unit 100 returns to the first position with instrument tab 220 of surgical instrument 200 fully seated in instrument tab seat 108d of adapter assembly 107, bottom surface 110f of locking arm 110b of tab lock 110 contacts upper surface 220a of instrument tab 220 so that finger 110d of tab lock 110 covers instrument tab seat 108d of adapter assembly 107 and secures instrument tab 220 of surgical instrument 200 within instrument tab seat 108d of adapter assembly 107. With instrument tab 220 of surgical instrument 200 secured within instrument tab seat 108d of adapter assembly 107, activation of motor assembly 103 causes instrument tab 220 to translate in the axial direction together with adapter assembly 107, as indicated by arrows "C." More specifically, activation of motor 104 of motor assembly 103 rotates shaft 106 of motor assembly 103 to axially drive adapter assembly 107, via threaded tube members 108h of adapter assembly 107, along shaft 106 of motor assembly 103. Axial movement of adapter assembly 107 imparts concomitant axial movement of instrument tab 220 of surgical instrument 200 relative to instrument body 210 of surgical instrument 200. As discussed above, axial movement of the instrument tab 220 of surgical instrument 200 causes end effector 202 of surgical instrument 200 to effectuate operation of end effector 202.

Figure 14:
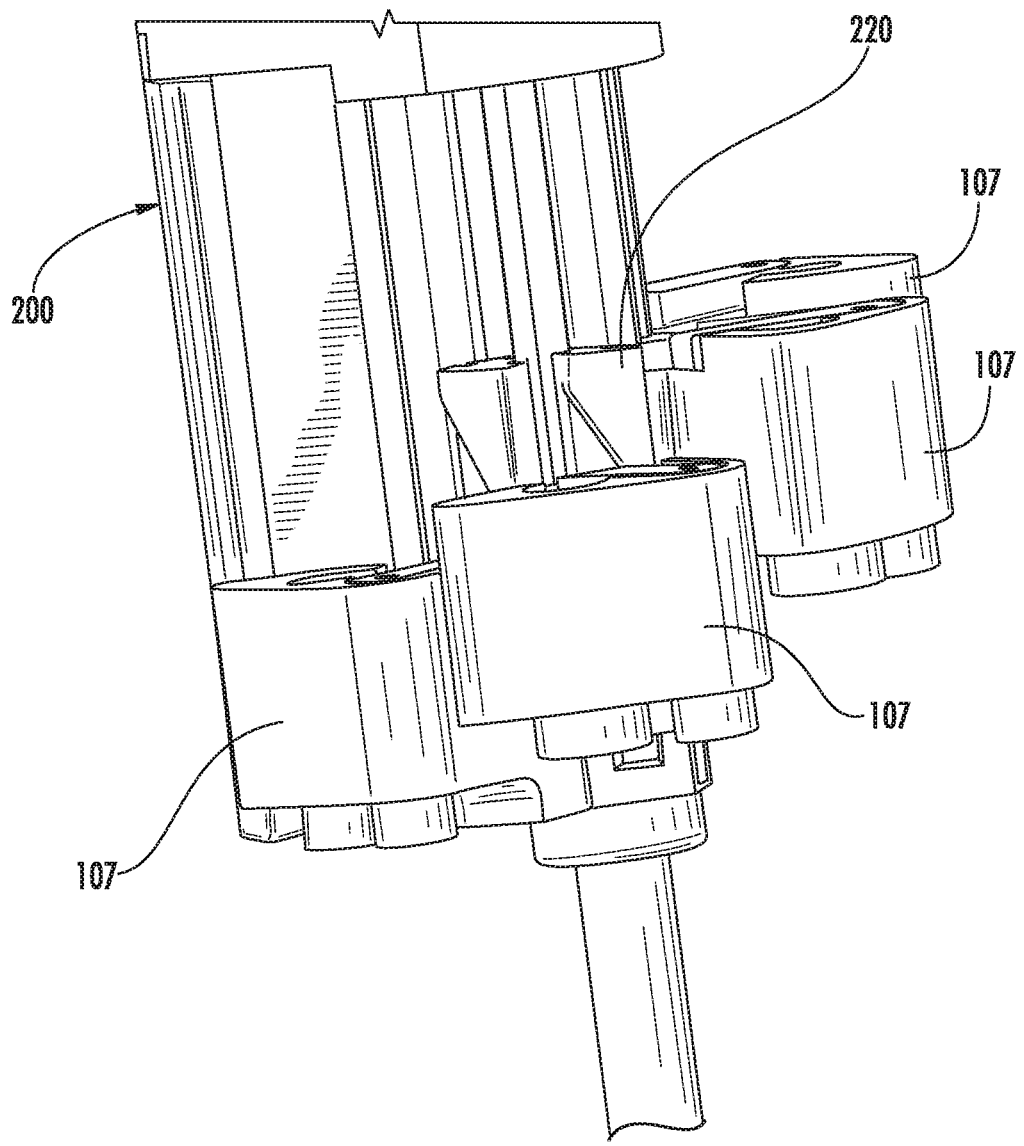

As seen in FIG. 14, any number of adapter assemblies 107 of instrument drive unit 100 can be coupled to respective instrument tabs 220 of surgical instrument 200 as described above to enable end effector 202 to perform various functions such as grasping, articulating, rotating, etc.

With reference to FIGS. 2-14, to release and/or uncouple one or more of the adapter assemblies 107 of instrument drive unit 100 from respective instrument tabs 220 of surgical instrument 200, tab locks 110 of respective adapter assemblies 107 can be manually and/or electronically rotated back toward the second position of tab lock 110 so that respective instrument tabs 220 of surgical instrument 200 can be separated from instrument tab seats 108d of respective adapter assemblies 107 of instrument drive unit 100. In embodiments, one or more components of adapter assembly 107 (e.g., one or more tube members 108h and/or tab locks 110 of adapter assembly 107) can include one more gears, teeth, bearings, springs, etc. that cooperate to enable motor assembly 103 of instrument drive unit 100 to electronically rotate one or more of tab locks 110. In some embodiments, one or more separate motor assemblies 103 may be coupled to, and/or engagable with, tab locks 110 to electronically rotate tab locks 110 relative to respective adapter bodies 108. In certain embodiments, adapter assemblies 107 may be advanced to an engagement gear (not shown) supported on shaft 106 of motor assembly 103 to engage a gearing assembly (not shown) associated with adapter body 108 and/or tab lock 110 for enabling motor assemblies 103 to electronically rotate tab locks 110.

Once each instrument tab 220 of surgical instrument 200 is separated from its respective adapter assembly 107, surgical instrument 200 can be separated from instrument drive unit 100; for example, to perform an instrument exchange.

One or more of the adapter assemblies 107 of the instrument drive unit 100 can be coupled to, and/or uncoupled from, their respective instrument tabs 220 of surgical instrument 200 independent of one or more of the other adapter assemblies 107. Additionally, and or alternatively, two or more of the adapter assemblies 107 can be coupled to, and/or uncoupled from, their respective instrument tabs 220 simultaneously.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A surgical system for selective connection to a robotic arm, the surgical system comprising:
an instrument drive unit including:
a motor assembly having a motor and a shaft extending from the motor; and
an adapter assembly connected to the shaft of the motor assembly and movable along the shaft, the adapter assembly including an adapter body and a tab lock supported by the adapter body;
and
a surgical instrument removably connectable to the instrument drive unit, the surgical instrument including an instrument body and an end effector supported by the instrument body, the instrument body supporting an instrument tab operatively associated with the end effector, the instrument tab of the surgical instrument engagable with the tab lock of the adapter assembly to move the tab lock relative to the adapter body of the adapter assembly from a first position to a second position as the adapter assembly moves relative to the instrument tab, the instrument tab configured to enable the tab lock to move from the second position to the first position so that the instrument tab secures to the adapter assembly.

2. The surgical system of claim 1, wherein the tab lock is rotatably supported in the adapter body.

3. The surgical system of claim 1, wherein the tab lock includes a spring configured to bias the tab lock toward the first position.

4. The surgical system of claim 1, wherein the adapter assembly and the instrument tab move together while the instrument tab is secured to the adapter assembly.

5. The surgical system of claim 1, wherein the instrument tab includes an angled surface, and wherein the tab lock is configured to cam along the angled surface of the instrument tab as the adapter assembly moves relative to the instrument tab.

6. The surgical system of claim 5, wherein the tab lock includes a shoulder that contacts the angled surface of the instrument tab to rotate the tab lock relative to the adapter body as the tab lock cams along the angled surface of the instrument tab.

7. The surgical system of claim 1, wherein the adapter body defines an instrument tab seat, the instrument tab receivable within the instrument tab seat to secure the instrument tab to the adapter body.

8. The surgical system of claim 1, wherein the instrument drive unit further includes a second adapter assembly coupled to a second motor assembly, and wherein the surgical instrument includes a second instrument tab, and wherein the second adapter assembly of the instrument drive unit is configured to secure to the second instrument tab of the surgical instrument.

9. The surgical system of claim 1, wherein the instrument drive unit has a drive unit body that defines a U-shaped opening, the U-shaped opening configured to receive the surgical instrument therein.

10. A robotic surgical assembly comprising:
a robotic arm;
a surgical instrument supporting an instrument tab; and
an instrument drive unit coupleable to the robotic arm, the instrument drive unit including:
a motor assembly having a motor and a shaft extending from the motor; and
an adapter assembly connected to the shaft of the motor assembly and movable along the shaft, the adapter assembly including an adapter body and a tab lock supported by the adapter body, the tab lock engagable with the instrument tab of the surgical instrument to move the tab lock relative to the adapter body from a first position to a second position as the adapter assembly moves relative to the instrument tab, the tab lock configured to move from the second position to the first position to secure the adapter assembly to the instrument tab of the surgical instrument.

11. The robotic surgical assembly of claim 10, wherein the tab lock is rotatably supported in the adapter body.

12. The robotic surgical assembly of claim 10, wherein the tab lock includes a spring configured to bias the tab lock toward the first position.

13. The robotic surgical assembly of claim 10, wherein the adapter assembly and the instrument tab move together while the instrument tab is secured to the adapter assembly.

14. The robotic surgical assembly of claim 10, wherein the instrument tab includes an angled surface, and wherein the tab lock is configured to cam along the angled surface of the instrument tab as the adapter assembly moves relative to the instrument tab.

15. The robotic surgical assembly of claim 14, wherein the tab lock includes a shoulder that contacts the angled surface of the instrument tab to rotate the tab lock relative to the adapter body as the tab lock cams along the angled surface of the instrument tab.

16. The robotic surgical assembly of claim 10, wherein the adapter body defines an instrument tab seat, the instrument tab receivable within the instrument tab seat to secure the instrument tab to the adapter body.

17. The robotic surgical assembly of claim 10, wherein the instrument drive unit further includes a second adapter assembly coupled to a second motor assembly, and wherein the surgical instrument includes a second instrument tab, and wherein the second adapter assembly of the instrument drive unit is configured to secure to the second instrument tab of the surgical instrument.

18. The robotic surgical assembly of claim 17, wherein the first and second instrument tabs are operatively associated with an end effector, and wherein the first and second instrument tabs are independently movable to operate the end effector.

19. The robotic surgical assembly of claim 10, wherein the instrument drive unit has a drive unit body that defines a U-shaped opening, the U-shaped opening configured to receive the surgical instrument therein.

20. A method for selectively coupling a surgical instrument to an instrument drive unit that is robotically controlled, the method comprising:
   advancing the surgical instrument into the instrument drive unit;
   camming a tab lock of an adapter assembly along an instrument tab of the surgical instrument as an adapter body of the adapter assembly moves relative to the instrument tab; and
   rotating the tab lock of the adapter assembly relative to the adapter body of the adapter assembly to secure the instrument tab to the adapter assembly so that the instrument tab moves with the adapter assembly along a longitudinal axis of the instrument drive unit.

\* \* \* \* \*